United States Patent [19]
Richmond

[11] Patent Number: 4,509,516
[45] Date of Patent: Apr. 9, 1985

[54] LIGAMENT TUNNELING INSTRUMENT

[75] Inventor: James W. Richmond, Comstock Township, Kalamazoo County, Mich.

[73] Assignee: Stryker Corporation, Kalamazoo, Mich.

[21] Appl. No.: 469,366

[22] Filed: Feb. 24, 1983

[51] Int. Cl.³ .............................................. A61B 17/00
[52] U.S. Cl. ................................................. 128/303 R
[58] Field of Search ..................... 128/303 R, 341, 328

[56] References Cited

U.S. PATENT DOCUMENTS 2,528,941 11/1950 Bassett et al. ................... 128/303 R
3,508,553 4/1970 Kanbar et al. ................... 128/303 R

FOREIGN PATENT DOCUMENTS 1546172 5/1979 United Kingdom ............ 128/303 R

Primary Examiner—Michael H. Thaler
Attorney, Agent, or Firm—Flynn, Thiel, Boutell & Tanis

[57] ABSTRACT

There is provided a surgical tool comprising an elongated rod of arcuate shape and a handle which is alternatively releasably affixable to one end or the other end of the rod. An eyelet for receiving an end of the anterior cruciate ligament implant or graft is provided in at least one of the ends of the rod. When the handle is connected to one end of the rod, the rod can be carefully pushed through the intercondyloid fossa of the femur from the anterior side to the posterior side thereof so as to thread it around the tissues therein and adjacent thereto, whereby to form a tunnel through the knee joint. Then the handle is removed from said one end and is connected to the other end of the rod. The implant is extended through the eyelet and then the rod is pulled through and beyond the posterior side whereby to draw the implant through the tunnel.

4 Claims, 7 Drawing Figures

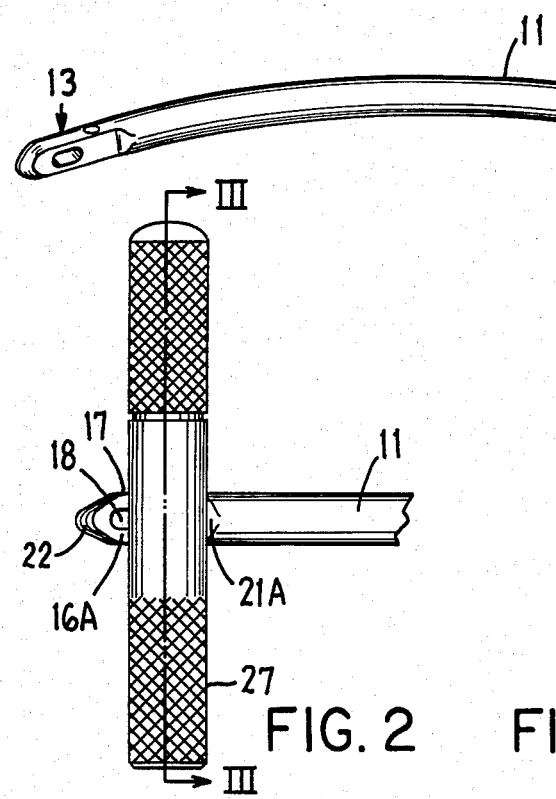
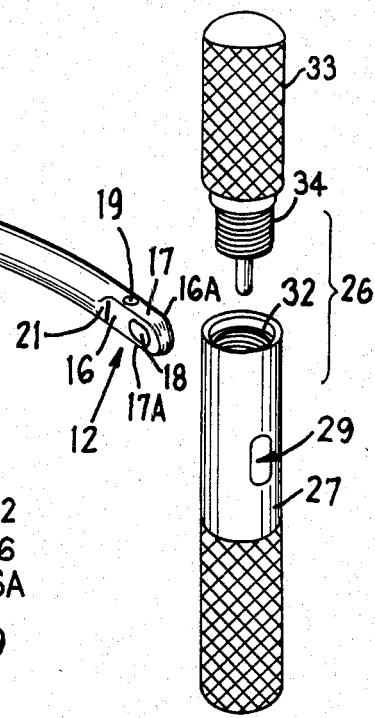
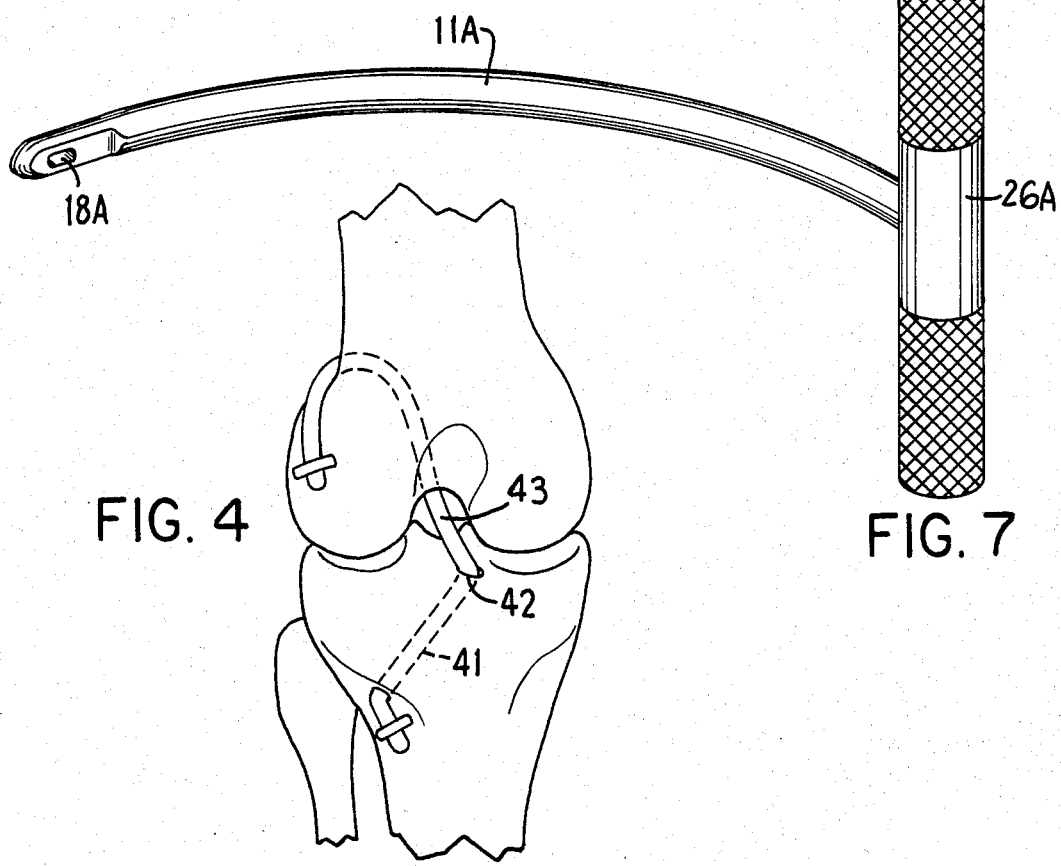
FIG. 1
FIG. 2  FIG. 3
FIG. 4
FIG. 7

LIGAMENT TUNNELING INSTRUMENT

This invention relates to a surgical instrument and, more particularly, relates to a ligament tunneling instrument useful, for example, in a surgical procedure for placing an autograft or an artificial anterior cruciate ligament implant prosthesis in the knee joint.

Although the surgical instrument according to the invention is widely useful for the general purpose of pulling autografts or artificial ligament implants through crowded regions in the human body, for illustrative purposes the following description will describe use of the instrument for pulling an anterior cruciate ligament implant through the knee joint. It will be understood, however, that the invention is not limited to this particular use of the surgical instrument.

In surgical procedures for reconstructing ligaments in the knee, the natural ligament is removed and an autograft or a bio-engineered artificial ligament implant is installed in its place. Materials useful to make bio-engineered artificial ligament implants include polyethylene terephthalate fibers (DACRON, a trademark of Du Pont), carbon fibers and other materials. In the following description, the term "ligament implant" shall include both autografts and artifical ligament implants.

The natural anterior cruciate ligament in the human body is attached to the depression in front of the intercondyloid eminence of the tibia. It extends upward and backward through the intercondyloid fossa of the femur, thence laterally toward the lateral condyle of the femur and is fixed to the medial and back part of the lateral condyle of the femur. The posterior cruciate ligament also passes through the intercondyloid fossa and crosses the anterior cruciate ligament therein in a manner similar to the lines of the letter X. Other parts of the knee joint, such as the medial meniscus and the lateral meniscus are located in front of, behind and/or within the region of the intercondyloid fossa of the femur.

It is very difficult to insert a ligament implant through the intercondyloid fossa of the femur because of the relatively small size of the fossa and the presence therein or closely adjacent thereto of other parts of the knee joint, as mentioned above. Thus, there is a need for a surgical instrument which can be used to insert a ligament implant through the intercondyloid fossa of the femur by a simple and safe procedure which can readily be performed by an orthopedic surgeon.

Accordingly, it is an object of this invention to provide a surgical instrument for inserting a ligament implant into the human body while minimizing the risk of injury to surrounding body tissue.

It is a further object of this invention to provide a surgical instrument, as aforesaid, which is useful to insert a ligament implant, such as an anterior cruciate ligament implant, through a crowded region of the body, such as the intercondyloid fossa of the femur.

It is a further object of the invention to provide a surgical instrument, as aforesaid, which can be extended from the anterior side of the knee joint through the intercondyloid fossa of the femur to the posterior side of the knee joint in order to form a tunnel through the tissues therein and which then can be used to pull an anterior cruciate ligament implant through the thus-formed tunnel so that said implant can then be attached to the posterior side of the lateral condyle of the femur.

Other objects and advantages of the invention will become apparent from the following description taken in conjunction with the attached drawings.

BRIEF DESCRIPTION OF THE DRAWINGS

FIG. 1 is an exploded, perspective view of the surgical instrument to which this invention relates.

FIG. 2 is a front view of one end of the surgical tool having the handle mounted thereon.

FIG. 3 is a sectional view taken along line III—III in FIG. 2.

FIG. 4 is a simplified, perspective view of the knee joint illustrating the manner of connecting the ligament implant thereto.

FIG. 7 is a view similar to FIG. 1 and illustrating a modification of the invention.

SUMMARY OF THE INVENTION

Figure 5:
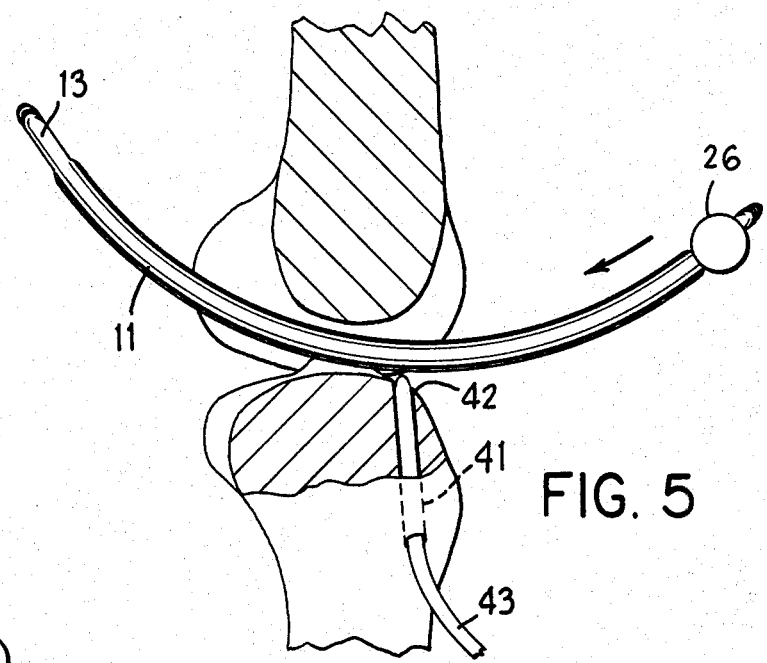
FIG. 5 is a simplified sectional view of the knee joint showing the use of the tool to form a tunnel for the artificial anterior cruciate ligament implant through the intercondyloid fossa and showing the implant itself disposed in a hole drilled through the upper extremity of the tibia.

According to the invention, there is provided a surgical tool comprising an elongated rod of arcuate shape in the lengthwise direction and a handle which is connected to one end of the rod. Preferably the handle is alternatively releasably affixable to the opposite ends of the rod. An eyelet for receiving an end of the ligament implant is provided in at least one of the ends of the rod. Preferably, the rod has eyelets at both ends thereof. The rod can be carefully pushed through the body joint, such as the intercondyloid fossa of the femur, so as to thread it between the tissues therein and adjacent thereto, whereby to form a tunnel. Then, the implant is extended through the eyelet and then the rod is pulled through and beyond the joint whereby to draw the implant through the tunnel.

DETAILED DESCRIPTION OF PREFERRED EMBODIMENTS

Referring to FIGS. 1 to 3, the surgical tool according to the invention is comprised of an elongated, smooth-surfaced rod 11 which, in plan view, has the shape of an arc of a circle of large diameter. The end portions 12 and 13 at the opposite ends of the rod 11 are shaped to define mountings for a handle, as further described hereinbelow. Except at the end portions 12 and 13, the rod has, in cross section, the shape of a closed smooth curve and is preferably of substantially circular cross section.

The end portions 12 and 13 of the rod 11 have the same shape. Accordingly, only end portion 12 will be described in detail herein and it will be understood that this description also applies to the end portion 13. At the end portion 12, material is removed from diametrically opposite sides of the rod 11 so as to form two flat, parallel, side surfaces 16 and 16A. The upper and lower surfaces 17 and 17A of the end portion 12 are slightly flattened so that the end portion 12, in cross section, is substantially rectangular with rounded corners (FIG. 3). An elongated hole 18 extends between and through the surfaces 16 and 16A and defines an eyelet for receiving the ligament implant, as described further hereinbelow. Although it is not essential also to provide an eyelet in end portion 13, it is preferred to do so for convenience so that the tool will be reversible. Further, a depression or cavity 19 is formed on the upper surface 17 of the end portion 12. A similar depression can be provided on the lower surface 17A of the end portion 12, if desired. Inclined surfaces 21 and 21A are provided at the inner ends of the flat side surfaces 16 and 16A to join those side surfaces smoothly with the remainder of the rod. Moreover, the outer end 22 of the end portion 12 of the rod 11 is shaped to form a smooth rounded cone having a rounded apex in order to facilitate insertion of the end of the rod 11 through the crowded region of the body, such as the intercondyloid fossa.

A handle 26 is detachably connectable to the rod at either end thereof. The handle 26 is comprised of a main handle part 27 which is of circular cross section. The main handle part 27 has a through slot 29 between its upper and lower ends, which slot is of substantially rectangular cross section and is adapted for slidably receiving the end portion 12 or 13 of the rod therethrough, as shown in FIG. 3. A hole 31 extends upwardly from the upper side of the slot 29 to an internally threaded cavity 32 which opens through the upper side of the main handle part 27. The locking part 33 of the handle has an externally threaded boss 34 which is thereadably receivable in the cavity 32. A pin 36 extends from the boss 34 and is receivable through the hole 31 into the depression 19 (FIG. 3). Thus, when the locking part 33 is threaded into the main handle part 27, the pin 36 extends into the depression 19 and locks the handle to the end portion of the rod 11. The inclined surfaces 21 and 21A act as stops in order to properly position the handle 27 so that the pin 36 is aligned with the depression 19. When thus assembled, the handle extends at a right angle to the rod in a manner similar to the crossbar of the letter T. The handle parts 27 and 33 are externally knurled to facilitate gripping thereof.

It will be observed that the handle 26 can alternatively be detachably secured to each of the end portions 12 and 13 of the rod 11 and that when thus secured, the handle does not rotate with respect to the rod, but rather, is removably fixedly attached thereto.

The rod and the handle are made of a material or materials suitable for use in surgical instruments, such as stainless steel. In one particular embodiment of the invention, the rod is made of 5/16 inch diameter stainless steel rod of circular cross section and it has an arcuate length of about 8 inches. Thus, it is capable of extending completely through and beyond the intercondyloid fossa of the femur, on the anterior and posterior sides thereof.

Referring to FIG. 4, there is schematically shown the mode of attaching an anterior cruciate ligament implant prosthesis to the knee joint. A hole 41 is drilled through the upper extremity of the tibia so that the upper end 42 of the hole 41 is located in front of the anterior intercondyloid fossa of the tibia. The anterior cruciate ligament implant 43 is threaded through the hole 41 and is then extended through a tunnel formed by the use of the surgical tool of this invention, as described below, so that the implant extends through the intercondyloid fossa of the femur. The posterior end portion of the implant is wrapped partway around the medial and lateral sides of the lateral condyle of the femur. Then, the ends of the implant are affixed to the tibia and the lateral condyle of the femur by suitable surgically acceptable fastening procedures, such as staples, bollards or the like.

Figure 6:
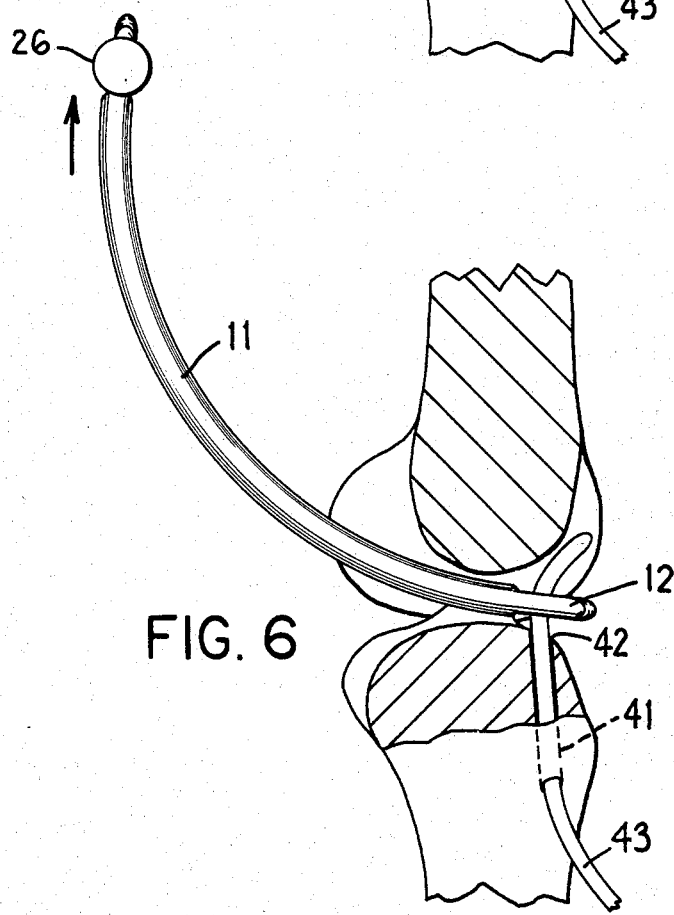
FIG. 6 is a view similar to FIG. 5 showing the tool connected to the upper end of the implant and ready to pull the implant through the tunnel to the posterior side of the knee joint.

Because of the presence of the posterior cruciate ligament, the lateral meniscus, the medial meniscus and other parts of the knee joint, it is very difficult to insert the anterior cruciate ligament implant through the intercondyloid fossa of the femur. The surgical tool, according to this invention, overcomes this difficulty by making it possible for the surgeon to form a tunnel through the intercondyloid fossa of the femur and then to draw the implant through that tunnel. As shown in FIG. 5, in order to form the tunnel, the handle 26 is attached to one end portion of the rod 11, here the end portion 12. Then the other end portion, here the end portion 13, is forced from the anterior side of the knee joint through the intercondyloid fossa of the femur by pushing on the rod 11 by means of the handle 26. Because the end of the end portion 13 is rounded and the end portion 13 is of reduced size, the surgeon can carefully thread the end portion 13 through the knee joint so as to avoid injury to other body tissue present thereat. Because the handle 26 is rigidly affixed to the rod, the surgeon can apply substantial pushing force to the rod 11 and can rotate the rod or change its angle of movement through the knee joint in order to enable the rod to pass between and around other parts of body tissue present in the knee joint. However, the size of the end portion 13 of the rod is sufficiently large that the end portion 13 will not penetrate through other body tissue present in or around the knee joint. Thus, forcing of the rod 11 through the intercondyloid fossa of the femur can be accomplished with greater ease and with a minimum risk of damage to other tissues present in the knee joint. After the rod 11 has been moved substantially to the position shown in FIG. 5, the handle 26 is detached from the end portion 12 on the anterior side of the knee joint and the handle is then attached to the end portion 13 of the rod which at this time is on the posterior side of the knee joint. The rod 11 is then pulled through the knee joint until the position shown in FIG. 6 is reached. At that time, the anterior cruciate ligament implant is passed through the eyelet 18 in the end portion 12 of the tool, in substantially the same manner that a thread is threaded through the eyelet of a sewing needle. Then the tool is pulled all the way through the knee joint so that the anterior cruciate ligament implant extends beyonds the posterior side of the knee joint. The tool is then detached from the implant and the ends of the implant are attached to the tibia and femur in the manner previously described.

Referring to FIG. 7, there is illustrated a modification in which the handle 26A is fixed to one end of the rod 11A and a single eyelet 18A is provided adjacent to the other end of the rod. In use of this modified tool, the rod 11A is pushed through the joint from the posterior side to the anterior side thereof, then the ligament implant is attached to the eyelet 18A and then the rod is pulled through the joint from the anterior side to the posterior side so that the ligament implant is threaded through the joint.

Thus, the tool according to the invention is useful for forming a tunnel through a joint, such as the intercondyloid fossa of the femur, and for drawing the ligament implant through that tunnel. The tool is strong and durable so that it will withstand vigorous usage, yet because of its smoothly rounded design, and the narrowed end portions, danger of injury to other parts of the knee joint is minimized. In the preferred embodiment of FIGS. 1 to 3, the tool is reversible so that either end thereof can be used as the posterior end and as the anterior end of the tool during use.

Although particular preferred embodiments of the invention have been described, the invention contemplates such changes or modifications therein as lie within the scope of the appended claims.

The embodiments of the invention in which an exclusive property or privilege is claimed are defined as follows:

1. A surgical instrument for inserting an anterior cruciate ligament implant through the intercondyloid fossa of the femur, comprising: an elongated rod and a handle attached to one end of said rod and extending transversely thereto so that the tool has the overall shape of the letter T, said rod being of circular cross section and being of arcuate shape in plan view so that said rod curves away from said handle in a direction toward the opposite end of said rod, said rod having substantially identical end portions at the opposite ends theeof, each of said end portions being of substantially rectangular cross section defined by two flat parallel side walls, an upper wall and a bottom wall, said side walls being laterally inwardly offset from the surface of said rod, said upper wall having a cavity therein, each of said end portions having an eyelet opening extending between and through said side walls, each of said eyelet openings being adapted to receive therethrough the end of an anterior cruciate ligament implant, the tips of said end portions being of smoothly rounded conical shape having a rounded apex so that said rod can be pushed through the intercondyloid fossa of the femur whereby to form a tunnel between the ligaments present in that portion of the knee joint, said handle being cylindrical and comprising an elongated main handle part and a locking part, said main handle part having a through-hole of substantially rectangular cross section between its upper and lower ends for slidably receiving one or the other of said end portions of said rod so that said handle cannot rotate with respect to said rod, said main handle part having an internally threaded recess opening through the upper side thereof and having a passage aligned with said cavity and extending between the upper side of said through-hole and the bottom of said internally threaded recess, said locking part having an externally threaded boss extending from its lower end and threaded into said internally threaded recess, and a pin extending downwardly from the lower end of said boss and extending through said passage into said cavity for releasably securing said handle to said rod, said handle being reversible from one end portion of said rod to the other end portion of said rod so that when said handle is releasably attached to one end portion of said rod, said rod can be pushed from the anterior side to the posterior side through the intercondyloid fossa of the femur to form said tunnel and then said handle can be detached from said one end portion of the rod and attached to the other end portion of the rod, the end of the anterior cruciate ligament implant can be passed through said eyelet opening in said one end portion of said rod and then said rod can be pulled through and beyond the posterior side of the intercondyloid fossa of the femur whereby said implant is moved through the tunnel to a location close to the posterior side of the lateral condyle of the femur.

2. A surgical instrument, comprising: an elongated, substantially rigid rod which is of arcuate shape in plane view, said rod having end portions at opposite ends thereof and a central portion extending between said end portions, said central portion having the cross-sectional shape of a closed smooth curve, said end portions being of reduced thickness relative to the thickness of said central portion and having an out-of-round cross section, each of said end portions having an eyelet therein extending transversely therethrough, the tips of each of said end portions being smoothly rounded so that said rod can be pushed through a joint in the human body, either end first, whereby to form a tunnel between the body tissue in and around that joint, each of said end portions having handle-attaching means thereon, and a handle releasably fixedly securable to said handle-attaching means on either of said end portions, said handle having a through-hole of out-of-round cross section and sized to slidably receive said end portions so that said handle cannot rotate with respect to said rod when said handle is mounted on one of said end portions.

3. A surgical instrument, comprising: an elongated, substantially rigid rod which is of arcuate shape in plan view, said rod having end portions at opposite ends thereof and a central portion extending between said end portions, said central portion having the cross-sectional shape of a closed smooth curve, said end portions being of reduced thickness relative to the thickness of said central portion, said end portions of said rod being of substantially identical size and structure, each of said end portions having two parallel flat side walls which are laterally inwardly offset from the wall of said central portion of said rod, said side walls being connected by upper and lower walls so that said end portions are substantially rectangular in cross section, each of said end portions having an eyelet opening therein extending between and through said side walls, the tips of each of said end portions being of smoothly rounded conical shape having a rounded apex so that said rod can be pushed through a joint in the human body, either end first, whereby to form a tunnel between the body tissue in and around that joint, each of said end portions having handle-attaching means thereon, and a handle releasably fixedly securable to said handle-attaching means on either of said end portions, said handle extending at a right angle to said rod and having between its ends a through-hole of substantially rectangular cross section for slidably receiving one of said end portions so that said handle cannot rotate with respect to said rod when said handle is mounted on one of said end portions.

4. A surgical instrument as claimed in claim 3 in which each of said end portions has a cavity in the upper wall thereof, and said handle comprises a main handle part and a locking part, said main handle part having said through-hole extending therethrough between its upper and lower ends, a passage extending upwardly from the upper side of said through-hole and communicating with an internally threaded recess in the upper end of said main handle part, said locking part having an externally threaded boss extending from its lower end and adapted to be threaded into said internally threaded recess, and a pin extending downwardly from the lower end of said boss and adapted to extend through said passage into said cavity for releasably securing said handle to said rod.

* * * * *